(12) United States Patent
Furudate et al.

(10) Patent No.: US 11,446,640 B2
(45) Date of Patent: Sep. 20, 2022

(54) VISIBLE-LIGHT-RESPONSIVE PHOTOCATALYTIC-TITANIUM-OXIDE-PARTICULATE DISPERSION LIQUID, MANUFACTURING METHOD THEREFOR, AND MEMBER HAVING THIN PHOTOCATALYTIC FILM ON SURFACE THEREOF

(71) Applicant: SHIN-ETSU CHEMICAL CO., LTD., Tokyo (JP)

(72) Inventors: Manabu Furudate, Kamisu (JP); Tomohiro Inoue, Kamisu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1186 days.

(21) Appl. No.: 15/560,901

(22) PCT Filed: Mar. 8, 2016

(86) PCT No.: PCT/JP2016/057047
§ 371 (c)(1),
(2) Date: Sep. 22, 2017

(87) PCT Pub. No.: WO2016/152487
PCT Pub. Date: Sep. 29, 2016

(65) Prior Publication Data
US 2018/0117567 A1    May 3, 2018

(30) Foreign Application Priority Data
Mar. 23, 2015 (JP) .............................. JP2015-059715

(51) Int. Cl.
| | | |
|---|---|---|
| *B01J 23/745* | (2006.01) | |
| *B01J 23/847* | (2006.01) | |
| *B01J 35/00* | (2006.01) | |
| *A61L 9/00* | (2006.01) | |
| *B01J 23/887* | (2006.01) | |
| *C09D 1/00* | (2006.01) | |
| *C09D 5/00* | (2006.01) | |
| *B01J 23/88* | (2006.01) | |
| *B01J 35/02* | (2006.01) | |
| *B01J 21/08* | (2006.01) | |
| *B01J 23/28* | (2006.01) | |
| *B01J 37/00* | (2006.01) | |
| *B01J 37/02* | (2006.01) | |

(Continued)

(52) U.S. Cl.
CPC .............. *B01J 23/745* (2013.01); *A61L 9/00* (2013.01); *B01J 21/08* (2013.01); *B01J 23/28* (2013.01); *B01J 23/8472* (2013.01); *B01J 23/88* (2013.01); *B01J 23/8875* (2013.01); *B01J 35/004* (2013.01); *B01J 35/0006* (2013.01); *B01J 35/02* (2013.01); *B01J 37/0018* (2013.01); *B01J 37/0215* (2013.01); *B01J 37/031* (2013.01); *B01J 37/04* (2013.01); *B01J 37/06* (2013.01); *B01J 37/10* (2013.01); *C09D 1/00* (2013.01); *C09D 5/00* (2013.01)

(58) Field of Classification Search
CPC .. B01J 23/745; B01J 23/8472; B01J 35/0006; B01J 23/8875; B01J 23/88; B01J 21/08; B01J 23/28; B01J 35/004; B01J 37/0018; B01J 37/0215; B01J 37/031; B01J 37/04; B01J 37/06; B01J 37/10; B01J 35/02; A61L 9/00; C09D 1/00; C09D 5/00
USPC ........................................................ 502/242
See application file for complete search history.

(56) References Cited

U.S. PATENT DOCUMENTS

| | | |
|---|---|---|
| 5,759,948 A | 6/1998 | Takaoka et al. |
| 8,603,302 B2 | 12/2013 | Hashimoto et al. |

(Continued)

FOREIGN PATENT DOCUMENTS

| | | |
|---|---|---|
| CN | 1327878 A | 12/2001 |
| JP | 07-303835 A | 11/1995 |

(Continued)

OTHER PUBLICATIONS

Wang et al, "Quantitative Determination of Titanium Lattice Defects and Solid-State Reaction Mechanism in Iron-Doped TiO2 Photocatalysts" 9692 J. Phys. Chem. B 2001, 105, 9692-9698 (Year: 2001).*

(Continued)

*Primary Examiner* — Colin W. Slifka
(74) *Attorney, Agent, or Firm* — Birch, Stewart, Kolasch & Birch, LLP

(57) ABSTRACT

As a visible-light-responsive photocatalytic-titanium-oxide-particulate dispersion liquid that can achieve a high visible light activity and is of a type different from the related art, the present invention provides a visible-light-responsive photocatalytic-titanium-oxide-particulate dispersion liquid in which two types of titanium oxide particulates are dispersed in an aqueous dispersion medium. The two types of titanium oxide particulates are first titanium oxide particulates, in which a tin component and a transition metal component (but excluding an iron-group component) for enhancing visible light responsiveness are dissolved, and second titanium oxide particulates, in which an iron-group component is dissolved. When a photocatalytic film formed by using this dispersion liquid is used, a high decomposition activity is achieved even in a case where a decomposition substrate has low concentration, which was previously difficult under visible light conditions.

15 Claims, No Drawings

(51) Int. Cl.
*B01J 37/03* (2006.01)
*B01J 37/04* (2006.01)
*B01J 37/06* (2006.01)
*B01J 37/10* (2006.01)

(56) References Cited

U.S. PATENT DOCUMENTS

| | | | |
|---|---|---|---|
| 9,604,198 B2 | 3/2017 | Furudate et al. | |
| 2001/0036897 A1 | 11/2001 | Tsujimichi et al. | |
| 2012/0214667 A1 | 8/2012 | Furudate et al. | |
| 2013/0168228 A1* | 7/2013 | Ozin | C25B 3/25 204/157.9 |
| 2014/0309103 A1* | 10/2014 | Furudate | B01J 23/8472 502/242 |
| 2016/0250621 A1 | 9/2016 | Furudate et al. | |

FOREIGN PATENT DOCUMENTS

| | | |
|---|---|---|
| JP | 2002-177775 A | 6/2002 |
| JP | 2009-148700 A | 7/2009 |
| JP | 2010-104913 A | 5/2010 |
| JP | 2011-136297 A | 7/2011 |
| JP | 2011-136879 A | 7/2011 |
| JP | 2012-210632 A | 11/2012 |
| JP | 2013-126654 A | 6/2013 |
| WO | WO 2007/026796 A1 | 3/2007 |
| WO | WO 2011/145385 A1 | 11/2011 |
| WO | WO-2013073320 A1 * 5/2013 .......... B01J 23/8472 |
| WO | WO 2014/045861 A1 | 3/2014 |
| WO | WO 2015/056556 A1 | 4/2015 |

OTHER PUBLICATIONS

Extended European Search Report dated Nov. 21, 2018, in European Patent Application No. 16768390.3.
International Search Report for PCT/JP2016/057047 (PCT/ISA/210) dated May 31, 2016.
Written Opinion of the International Searching Authority for PCT/JP2016/057047 (PCT/ISA/237) dated May 31, 2016.
Office Action dated Nov. 13, 2019, in Chinese Patent Application No. 201680017535.7.

* cited by examiner

VISIBLE-LIGHT-RESPONSIVE PHOTOCATALYTIC-TITANIUM-OXIDE-PARTICULATE DISPERSION LIQUID, MANUFACTURING METHOD THEREFOR, AND MEMBER HAVING THIN PHOTOCATALYTIC FILM ON SURFACE THEREOF

TECHNICAL FIELD

The present invention relates to a visible light-responsive photocatalytic titanium oxide fine particle dispersion, a method for producing such a dispersion, and a member having on a surface thereof a photocatalytic thin film formed using such a dispersion. More particularly, the invention relates to a visible light-responsive photocatalytic titanium oxide fine particle dispersion from which a photocatalytic thin film of high transparency that manifests a photocatalytic activity even on exposure only to visible light (400 to 800 nm) can easily be produced, a method for producing such a dispersion, and a member having on a surface thereof a photocatalytic thin film formed using such a dispersion.

BACKGROUND ART

Photocatalytic titanium oxide fine particles are frequently used in such applications as the cleaning, deodorization and disinfecting of substrate surfaces. As used herein, a "photocatalytic reaction" refers to a reaction caused by excited electrons and holes generated due to the absorption of light by titanium oxide. The decomposition of organic matter is thought to arise primarily by mechanisms such as the following: (1) the excited electrons and holes that have formed carry out oxidation-reduction reactions with oxygen and water adsorbed to the titanium oxide surface, generating active species which decompose organic matter; and (2) the holes that have formed directly oxidize and decompose organic matter adsorbed to the titanium oxide surface.

Studies have been carried out recently to attempt to apply such photocatalysis not only to outdoor uses where ultraviolet light can be utilized, but also to indoor spaces illuminated with light sources such as fluorescent lamps that produce light primarily in the visible range (wavelength, 400 to 800 nm). For example, a tungsten oxide photocatalytic body has been disclosed as a visible light-responsive photocatalyst (JP-A 2009-148700), but because tungsten is a scarce element, there exists a desire for improvements in the visible light activity of photocatalysts that utilize the widely available element titanium.

Methods for increasing the visible light activity of photocatalysts which use titanium oxide include the method of supporting iron or copper on the surface of titanium oxide fine particles or metal-doped titanium oxide fine particles (see, for example, JP-A 2012-210632: Patent Document 2; and JP-A 2010-104913: Patent Document 3), and a method which separately prepares titanium oxide fine particles containing in solid solution (doped with) tin and a transition metal that increases the visible light activity and titanium oxide fine particles containing in solid solution copper and then uses these separately prepared particles in admixture (WO 2014/045861: Patent Document 4).

The latter of these (Patent Document 4), that is, the method which separately prepares titanium oxide fine particles containing in solid solution tin and a transition metal that increases the visible light activity and titanium oxide fine particles containing in solid solution copper and then uses these separately prepared particles in admixture, has the advantage that because the metals used other than titanium are contained in solid solution within the titanium oxide particles, the particles are stable and do not readily deteriorate, enabling a photocatalytic thin film of high durability to be obtained.

PRIOR ART DOCUMENTS

Patent Documents

Patent Document 1: JP-A 2009-148700
Patent Document 2: JP-A 2012-210632
Patent Document 3: JP-A 2010-104913
Patent Document 4: WO 2014/045861
Patent Document 5: JP-A H07-303835

SUMMARY OF THE INVENTION

Problems to be Solved by the Invention

An object of this invention is to provide, by combining and mixing together titanium oxide fine particles containing in solid solution different transition metals, a visible light-responsive photocatalytic titanium oxide fine particle dispersion which can obtain a high visible light activity differing from that of the prior art. Further objects are to provide a method of producing such a dispersion, and a member having on a surface thereof a photocatalytic thin film formed using such a dispersion.

Means for Solving the Problems

One approach taken by the inventors to achieve the above objects has been to conduct a search for novel materials that exhibit a high photocatalytic activity only under visible light conditions by varying the second type of titanium oxide fine particle which is combined with the first type of titanium oxide fine particle titanium oxide fine particles, used in Patent Document 4, containing in solid solution tin and a transition metal that increases the visible light activity. In the course of this investigation, although the titanium oxide fine particles containing a copper constituent in solid solution which are the second type of titanium oxide fine particle used in Patent Document 4 exhibit some photocatalytic activity even under visible light (400 to 800 nm) only conditions, the inventors have found that, surprisingly, when titanium oxide fine particles containing an iron constituent in solid solution—which particles by themselves exhibit substantially no photocatalytic activity under visible light only conditions—are included as the second type of titanium oxide fine particle, a high photocatalytic activity comparable to that obtained from combination with titanium oxide fine particles containing a copper constituent in solid solution is exhibited under visible light only conditions.

The inventors conducted further investigations on including such titanium oxide fine particles containing an iron constituent in solid solution as the second type of titanium oxide fine particle, whereupon they found that when acetaldehyde gas contained within air is decomposed under visible light, a decomposition activity can be obtained even in low-concentration regions for which such activity has been difficult to obtain using conventional materials. Specifically, it was possible, under visible light conditions and within a significantly short time, to reduce the level to the indoor concentration guideline value of 0.03 ppm or below for a chemical substance (acetaldehyde) within indoor air established by the Japanese Ministry of Health, Labor and Welfare. That is, the inventors have discovered that, by using a photocatalytic film formed using a visible light-responsive photocatalytic titanium oxide fine particle dispersion containing a first type of titanium oxide fine particle containing in solid solution tin and a transition metal that increases the visible light activity and a second type of titanium oxide fine particle containing in solid solution an iron group constituent, a high decomposition activity can be obtained even in cases where the decomposition substrate has a low concentration at which obtaining such activity under visible light conditions has hitherto been difficult.

Accordingly, this invention provides the following visible light-responsive photocatalytic titanium oxide fine particle, method of production therefor, and member having on a surface thereof a photocatalytic thin film formed using such a dispersion.

[1] A visible light-responsive photocatalytic titanium oxide fine particle dispersion containing two types of titanium oxide fine particles dispersed in an aqueous dispersion medium: a first type of titanium oxide fine particle which contains in solid solution a tin constituent and a transition metal constituent (exclusive of iron group constituents) that increases visible light responsiveness, and a second type of titanium oxide fine particle which contains in solid solution an iron group constituent.

[2] The visible light-responsive photocatalytic titanium oxide fine particle dispersion of [1], wherein the content of the tin constituent in the first type of titanium oxide fine particle, expressed as a molar ratio with titanium (Ti/Sn), is from 1 to 1,000.

[3] The visible light-responsive photocatalytic titanium oxide fine particle dispersion of [1] or [2], wherein the transition metal constituent in solid solution within the first type of titanium oxide fine particle is at least one selected from the group consisting of vanadium, chromium, manganese, niobium, molybdenum, rhodium, antimony, tungsten and cerium.

[4] The visible light-responsive photocatalytic titanium oxide fine particle dispersion of [1] or [2], wherein the transition metal constituent in solid solution within the first type of titanium oxide fine particle is at least one selected from the group consisting of molybdenum and vanadium.

[5] The visible light-responsive photocatalytic titanium oxide fine particle dispersion of [4], wherein the content of the molybdenum constituent within the first type of titanium oxide fine particle, expressed as a molar ratio with titanium (Ti/Mo), is from 1 to 1,000 and the content of the vanadium constituent, expressed as a molar ratio with titanium (Ti/V) is from 10 to 10,000.

[6] The visible light-responsive photocatalytic titanium oxide fine particle dispersion of any of [1] to [5], wherein the content of the iron group constituent within the second type of titanium oxide fine particle, expressed as a molar ratio with titanium (Ti/iron group constituent), is from 1 to 1,000.

[7] The visible light-responsive photocatalytic titanium oxide fine particle dispersion of any of [1] to [6], wherein the iron group constituent in solid solution within the second type of titanium oxide fine particle is an iron constituent.

[8] The visible light-responsive photocatalytic titanium oxide fine particle dispersion of any of [1] to [7], wherein the first type of titanium oxide fine particle and the second type of titanium oxide fine particle have a mixing ratio therebetween, expressed as the weight ratio [(first type of titanium oxide fine particle)/(second type of titanium oxide fine particle)], of from 99 to 0.01.

[9] The visible light-responsive photocatalytic titanium oxide fine particle dispersion of any of [1] to [8], further comprising a binder.

[10] The visible light-responsive photocatalytic titanium oxide fine particle dispersion of [9], wherein the binder is a silicon compound-based binder.

[11] A member having on a surface thereof a photocatalytic thin film formed by using the visible light-responsive photocatalytic titanium oxide fine particle dispersion of any of [1] to [10].

[12] A method for producing a visible light-responsive photocatalytic titanium oxide fine particle dispersion, comprising the steps of:

(1) preparing a tin and transition metal-containing peroxotitanic acid solution from a starting titanium compound, a tin compound, a transition metal compound (exclusive of iron group compounds), a basic substance, hydrogen peroxide and an aqueous dispersion medium;

(2) preparing a tin and transition metal-containing titanium oxide fine particle dispersion by heating the tin and transition metal-containing peroxotitanic acid solution prepared in Step (1) at from 80 to 250° C. under pressure control;

(3) preparing an iron group element-containing peroxotitanic acid solution from a starting titanium compound, an iron group compound, a basic substance, hydrogen peroxide and an aqueous dispersion medium;

(4) preparing an iron group element-containing titanium oxide fine particle dispersion by heating the iron group element-containing peroxotitanic acid solution prepared in Step (3) at from 80 to 250° C. under pressure control; and (5) mixing together the two titanium oxide fine particle dispersions prepared in Steps (2) and (4).

Advantageous Effects of the Invention

This invention makes it possible to provide a visible light-responsive photocatalytic titanium oxide fine particle dispersion from which there can easily be produced a photocatalytic thin film of high transparency that manifests a photocatalytic activity even when exposed only to visible light (400 to 800 nm), a method for producing such a dispersion, and a member having on a surface thereof a photocatalytic thin film formed using such a dispersion.

EMBODIMENT FOR CARRYING OUT THE INVENTION

The visible light-responsive photocatalytic titanium oxide fine particle dispersion, method for producing such a dispersion, and member having a photocatalytic thin film on a surface thereof of the invention are described more fully below.

<Visible Light-Responsive Photocatalytic Titanium Oxide Fine Particle Dispersion>

The visible light-responsive photocatalytic titanium oxide fine particle dispersion of the invention is made up of titanium oxide fine particles of differing compositions—referred to herein as a "first type" of titanium oxide fine particle and a "second type" of titanium oxide fine particle—that are dispersed in an aqueous dispersion medium. Titanium oxide fine particles of the first type are titanium oxide fine particles containing in solid solution a tin constituent and a transition metal constituent (exclusive of iron group constituents), and titanium oxide fine particles of the second type are titanium oxide fine particles containing in solid solution an iron group constituent.

As used herein, "solid solution" refers to a phase in which atoms at lattice points in one given crystal phase are substituted with other atoms or in which other atoms have entered into lattice interstices; that is, it refers to a mixed phase which can be thought of as a given crystal phase having another substance dissolved therein, the crystal phase being understood here to be a homogeneous phase. A solid solution in which solvent atoms at lattice points are substituted with solute atoms is called a "substituted solid solution," and a solid solution in which solute atoms have entered into lattice interstices is called an "interstitial solid solution." Here, "solid solution" may refer to either of these.

The titanium oxide fine particles of the invention are characterized by, in the first type of titanium oxide fine particle, the formation of a solid solution with tin and a transition metal atom (exclusive of iron group constituents) and, in the second type of titanium oxide fine particle, the formation of a solid solution with an iron group constituent. The solid solution may be either a substituted solid solution or an interstitial solid solution. A substituted solid solution is one that forms with the substitution of various metal atoms at titanium sites in the titanium oxide crystals, and an interstitial solid solution is one that forms with the entry of various metal atoms into lattice interstices in the titanium oxide crystals. When various metal atoms enter into solid solution in titanium oxide, in measurement of the crystal phase by x-ray diffraction analysis or the like, only peaks for the crystal phase of titanium oxide are observed; peaks for compounds attributable to the various metal atoms that were added are not observed.

Methods of forming solid solutions of different metals in metal oxide crystals include, without particular limitation, vapor phase methods (e.g., chemical vapor deposition, physical vapor deposition), liquid phase methods (e.g., hydrothermal method, sol-gel method), and solid phase methods (e.g., high-temperature firing).

Titanium oxide fine particles are generally known to have three crystal phases: rutile, anatase and brookite. The use of chiefly rutile and anatase in both the first type of titanium oxide fine particle and the second type of titanium oxide fine particle is preferred. In addition, of rutile and anatase, it is preferable for the first type of titanium oxide fine particle to be chiefly rutile and it is preferable for the second type of titanium oxide fine particle to be chiefly anatase. "Chiefly" refers here to generally at least 50 wt %, preferably at least 70 wt %, and more preferably at least 90 wt %, and may even be 100 wt %, of all the titanium oxide fine particle crystals.

The dispersion medium used in the dispersion is typically an aqueous solvent, with the use of water being preferred, although a mixed solvent of water and a hydrophilic organic solvent that mixes with water in any ratio may be used. The water is preferably, for example, deionized water, distilled water, or purified water. The hydrophilic organic solvent is preferably, for example, an alcohol such as methanol, ethanol or isopropanol; a glycol such as ethylene glycol; or a glycol ether such as ethylene glycol monomethyl ether, ethylene glycol monoethyl ether or propylene glycol n-propyl ether. When a mixed solvent is used, the ratio of hydrophilic organic solvent in the mixed solvent is preferably more than 0 and 50 wt % or less, more preferably 20 wt % or less, and even more preferably 10 wt % or less.

The first type of titanium oxide fine particle is a titanium oxide fine particle which contains in solid solution a tin constituent and a transition metal constituent other than iron group constituents that increases the visible light activity. The transition metal constituent that increases the visible light activity can be selected from among vanadium, chromium, manganese, niobium, molybdenum, rhodium, antimony, tungsten and cerium. Of these, the selection of molybdenum and/or vanadium is preferred.

The tin constituent that forms a solid solution in the first type of titanium oxide fine particle is for increasing the visible light responsiveness of the photocatalytic thin film, and may be any tin constituent derived from a tin compound, such as tin metal (Sn), oxides (SnO, $SnO_2$), hydroxides, chlorides ($SnCl_2$, $SnCl_4$), nitrates ($Sn(NO_3)_2$), sulfates ($SnSO_4$), halides and complex compounds. These may be used singly or two or more may be used in combination. Of these, the use of oxides (SnO, $SnO_2$), chlorides ($SnCl_2$, $SnCl_4$) or sulfates ($SnSO_4$) is preferred.

The content of tin constituent in the first type of titanium oxide fine particle, expressed as a molar ratio with titanium (Ti/Sn), is from 1 to 1,000, preferably from 5 to 500, and more preferably from 5 to 100. When the molar ratio is less than 1, the titanium oxide content decreases and a sufficient photocatalytic effect may not be exhibited. When the molar ratio is greater than 1,000, the visible light responsiveness may be inadequate.

The transition metal constituent contained in solid solution within the first type of titanium oxide fine particle may be any that is derived from compounds of the transition metal, such as the metal, oxides, hydroxides, chlorides, nitrates, sulfates, halides and various complex compounds. These may be used singly or two or more may be used together.

The content of the transition metal constituent in the first type of titanium oxide fine particle may be suitably selected according to the type of transition metal constituent although, expressed as the molar ratio with titanium (Ti/transition metal), the content is preferably in the range of 1 to 10,000, and especially the range of 5 to 1,000.

Here, when molybdenum is selected as the transition metal constituent to be included in solid solution within the first type of titanium oxide fine particle, the molybdenum constituent may be any that is derived from molybdenum compounds, examples of which include molybdenum metal (Mo), oxides ($MoO_2$, $MoO_3$), hydroxides, chlorides ($MoCl_3$, $MoCl_5$), nitrates, sulfates, halides and complex compounds. These may be used singly or two or more may be used in combination. Of these, the use of oxides ($MoO_2$, $MoO_3$) or chlorides ($MoCl_3$, $MoCl_5$) is preferred.

The content of the molybdenum constituent in the first type of titanium oxide fine particle, expressed as the molar ratio with titanium (Ti/Mo), is from 1 to 1,000, preferably from 2 to 100, and more preferably from 2 to 50. The reason for this range is that at a molar ratio below 1, the titanium oxide content becomes low and a sufficient photocatalytic effect may not be exhibited, and at a molar ratio greater than 1,000, the visible light responsiveness may be inadequate and a high decomposition activity at low concentrations of acetaldehyde may not be obtained.

When vanadium is selected as the transition metal constituent to be included in solid solution within the first type of titanium oxide fine particle, the vanadium constituent may be any that is derived from vanadium compounds, examples of which include vanadium metal (V), oxides (VO, $V_2O_3$, $VO_2$, $V_2O_5$), hydroxides, chlorides ($VCl_5$), the oxychloride ($VOCl_3$), nitrates, sulfates, the oxysulfate ($VOSO_4$), halides and complex compounds. These may be used singly or two or more may be used in combination. Of these, the use of oxides ($V_2O_3$, $V_2O_5$), chlorides ($VCl_5$), the oxychloride ($VOCl_3$) or the oxysulfate ($VOSO_4$) is preferred.

The content of the vanadium constituent in the first type of titanium oxide fine particle, expressed as the molar ratio with titanium (Ti/V) is from 10 to 10,000, preferably from 100 to 10,000, and more preferably from 100 to 5,000. The reason for this range is that at a molar ratio below 10, the titanium oxide crystal content becomes low and a sufficient photocatalytic effect may not be exhibited, and at a molar ratio greater than 10,000, the visible light responsiveness may be inadequate and a high decomposition activity at low concentrations of acetaldehyde may not be obtained.

Molybdenum and vanadium may both be selected as the transition metal constituent included in the first type of titanium oxide fine particle. Their respective contents in this case may be selected from the above ranges, provided that the molar ratio between the sum of these contents and titanium, expressed as [Ti/(Mo+V)], is 1 or more but smaller than 10,000.

The first type of titanium oxide fine particle may be of one kind used alone, or may be of two or more kinds used in combination. When two or more kinds of differing visible light responsivenesses are combined, a visible light activity-increasing effect may be obtained.

The second type of titanium oxide fine particle has a composition that differs from that of the first type of titanium oxide fine particle, and is characterized by containing in solid solution an iron group constituent. The general form is one which, unlike the first type of titanium oxide fine particle, includes no tin and no transition metal other than an iron group constituent.

Iron group metals contained in solid solution within the second type of titanium oxide fine particle are exemplified by iron, cobalt and nickel. Of these, iron is preferred.

The iron group constituent included in solid solution within the second type of titanium oxide fine particle may be any that is derived from iron group compounds, such as iron metal (Fe), oxides ($Fe_2O_3$, $Fe_3O_4$), hydroxides (FeO(OH)), chlorides ($FeCl_2$, $FeCl_3$), nitrates ($Fe(NO_3)_3$), sulfates ($FeSO_4$, $Fe_2(SO_4)_3$), halides and complex compounds. These may be used singly or two or more may be used in combination. Of these, the use of oxides ($Fe_2O_3$, $Fe_3O_4$), hydroxides (FeO(OH)), chlorides ($FeCl_2$, $FeCl_3$), nitrates ($Fe(NO_3)_3$) and sulfates ($FeSO_4$, $Fe_2(SO_4)_3$) is preferred.

The content of the iron group constituent in the second type of titanium oxide fine particle, expressed as the molar ratio with titanium (Ti/iron group constituent) is from 1 to 1,000, preferably from 2 to 200, and more preferably from 5 to 100. The reason for this range is that at a molar ratio below 1, the titanium oxide content becomes low and a sufficient photocatalytic effect may not be exhibited, and at a molar ratio greater than 1,000, the visible light responsiveness may be inadequate.

The first type of titanium oxide fine particle and second type of titanium oxide fine particle in the visible light-responsive photocatalytic titanium oxide fine particle dispersion have a volume-based 50% cumulative distribution size ($D_{50}$) measured by dynamic laser light scattering (which size is also referred to below as the "average particle size") of preferably from 5 to 30 nm, and more preferably from 5 to 20 nm. This is because, at an average particle size below 5 nm, the photocatalytic activity may be inadequate, and at more than 30 nm, the dispersion may become opaque. Instruments that may be used to measure the average particle size include, for example, the Nanotrac UPA-EX150 (Nikkiso Co., Ltd.) and the LA-910 (Horiba, Ltd.).

The first type of titanium oxide fine particle and the second type of titanium oxide fine particle included in the visible light-responsive photocatalytic titanium oxide fine particle dispersion have a mixing ratio therebetween, expressed as the weight ratio [(first type of titanium oxide fine particle)/(second type of titanium oxide fine particle)], of preferably from 99 to 0.01, more preferably from 19 to 0.05, and even more preferably from 9 to 1. This is because, at a weight ratio in excess of 99 or below 0.01, the visible light activity may be inadequate.

From the standpoint of the ease of producing a photocatalytic thin film of the required thickness, the combined concentration of the first type of titanium oxide fine particle and the second type of titanium oxide fine particle in the visible light-responsive photocatalytic titanium oxide fine particle dispersion is preferably from 0.01 to 20 wt %, and especially from 0.5 to 10 wt %.

In addition, a binder may be added to the visible light-responsive photocatalytic titanium oxide fine particle dispersion, both for the purpose of making the dispersion easier to apply to the surface of the subsequently described various types of members and also to make the fine particles readily adhering. Examples of binders include silicon, aluminum, titanium, zirconium and other metal compound-based binders, and fluoroplastic, acrylic resin, urethane resin and other organic resin-based binders.

The binder is added and used in a weight ratio between the binder and the titanium oxide, expressed as (binder/titanium oxide), of preferably from 0.01 to 99, more preferably from 0.1 to 9, and even more preferably from 0.4 to 2.5. The reason is that, at a weight ratio below 0.01, adherence of the titanium oxide fine particles to the surface of various types of members may be inadequate, and at a weight ratio above 99, the visible light activity may be inadequate.

In particular, to obtain an excellent photocatalytic thin film having a high photocatalysis and transparency, it is especially desirable for a silicon compound-based binder to be added and used in a compounding ratio (weight ratio between silicon compound and titanium oxide) of preferably from 1:99 to 99:1, more preferably from 10:90 to 90:10, and even more preferably from 30:70 to 70:30. Here, "silicon compound-based binder" refers to a colloidal dispersion, solution or emulsion of a silicon compound that is obtained by including a solid or liquid silicon compound in an aqueous dispersion medium. Illustrative examples include colloidal silica (preferred particle size, 1 to 150 nm); solutions of silicates: silane and siloxane hydrolyzate emulsions; silicone resin emulsions; and emulsions of copolymers of a silicone resin with another resin, such as silicone-acrylic resin copolymers and silicone-urethane resin copolymers.

<Method for Producing Visible Light-Responsive Photocatalytic Titanium Oxide Fine Particle Dispersion>

The visible light-responsive photocatalytic titanium oxide fine particle dispersion of the invention is produced by preparing both a dispersion of the first type of titanium oxide fine particle (first titanium oxide fine particle dispersion) and a dispersion of the second type of titanium oxide fine particle (second titanium oxide fine particle dispersion), and then mixing together the first titanium oxide fine particle dispersion and the second titanium oxide fine particle dispersion.

This is exemplified by a production method that includes the following Steps (1) to (5):

(1) preparing a tin and transition metal-containing peroxotitanic acid solution from a starting titanium compound, a tin compound, a transition metal compound (exclusive of iron group compounds), a basic substance, hydrogen peroxide and an aqueous dispersion medium;

(2) preparing a tin and transition metal-containing titanium oxide fine particle dispersion by heating the tin and transition metal-containing peroxotitanic acid solution prepared in Step (1) at from 80 to 250° C. under pressure control;

(3) preparing an iron group element-containing peroxotitanic acid solution from a starting titanium compound, an iron group compound, a basic substance, hydrogen peroxide and an aqueous dispersion medium;

(4) preparing an iron group element-containing titanium oxide fine particle dispersion by heating the iron group element-containing peroxotitanic acid solution prepared in Step (3) at from 80 to 250° C. under pressure control; and (5) mixing together the two titanium oxide fine particle dispersions prepared in Steps (2) and (4).

Steps (1) and (2) are steps for obtaining the first titanium oxide fine particle dispersion, Steps (3) and (4) are steps for obtaining the second titanium oxide fine particle dispersion, and Step (5) is a final step for obtaining a dispersion containing both the first type of titanium oxide fine particle and the second type of titanium oxide fine particle.

As already mentioned, it is preferable to utilize molybdenum compounds and/or vanadium compounds as the transition metal compounds used in Step (1). This is the premise under which each of the steps is described in detail below.

Step (1):

In Step (1), a transition metal and tin-containing peroxotitanic acid solution is prepared by reacting a starting titanium compound, a transition metal compound, a tin compound, a basic substance and hydrogen peroxide in an aqueous dispersion medium.

The reaction method may be either a method that adds the basic substance to the starting titanium compound within the aqueous dispersion medium to form titanium hydroxide, removes impurity ions other than the metallic ions included, adds hydrogen peroxide to form peroxotitanic acid, and then adds the transition metal compound and the tin compound, thereby giving a transition metal and tin-containing peroxotitanic acid solution; or a method that adds the transition metal compound and the tin compound to the starting titanium compound and the basic substance within an aqueous dispersion medium and effects dissolution so as to form a transition metal and tin-containing titanium hydroxide, removes impurity ions other than the metallic ions included, and subsequently adds hydrogen peroxide, thereby giving a transition metal and tin-containing peroxotitanic acid solution.

Moreover, in the first stage of the latter method, the starting titanium compound and the basic substance within the aqueous dispersion medium may be separated into two aqueous dispersion media (two liquids), such as an aqueous dispersion medium in which the starting titanium compound is dispersed and an aqueous dispersion medium in which the basic substance is dispersed, and the transition metal compound and the tin compound may be dissolved in one or both of these two liquids, depending on the solubilities of the respective compounds in the two liquids, after which both solutions may be mixed together.

After a transition metal and tin-containing peroxotitanic acid solution is thus obtained, the solution is furnished to the hydrothermal reaction in subsequently described Step (2), thus enabling titanium oxide fine particles in which these respective metals are present in solid solution with titanium oxide to be obtained.

Examples of the starting titanium compound include inorganic acid salts of titanium, such as chlorides, nitrates, and sulfates; organic acid salts such as the titanium salts of formic acid, citric acid, oxalic acid, lactic acid and glycolic acid; and the titanium hydroxide that settles out when hydrolysis is carried out by adding an alkali to aqueous solutions of these. Such starting titanium compounds may be used singly or two or more may be used in combination. Of these, the use of titanium chlorides ($TiCl_3$, $TiCl_4$) is preferred.

The transition metal compound, the tin compound and the aqueous dispersion medium, each of which has been described above, are used by being compounded in the foregoing manner. The concentration of the starting titanium compound aqueous solution formed of the starting titanium compound and the aqueous dispersion medium is preferably 60 wt % or less, and more preferably 30 wt % or less. The concentration lower limit is set as appropriate, although a concentration of at least 1 wt % is generally preferred.

The purpose of the basic substance is to smoothly convert the starting titanium compound into titanium hydroxide. Illustrative examples include hydroxides of alkali metals or alkaline earth metals, such as sodium hydroxide and potassium hydroxide; and amine compounds such as ammonia, alkanolamines and alkylamines. The basic substance is added and used in an amount such as to bring the pH of the aqueous solution of the starting titanium compound to 7 or above, and especially from 7 to 10. The basic substance may be used together with the aqueous dispersion medium after first being rendered into an aqueous solution of a suitable concentration.

The purpose of the hydrogen peroxide is to convert the starting titanium compound or titanium hydroxide into peroxotitanium, that is, a titanium oxide compound containing a Ti—O—O—Ti bond, and is typically used in the form of hydrogen peroxide water. The amount of hydrogen peroxide added is preferably set to from 1.5 to 20 moles per mole of transition metal, vanadium and tin combined. When adding hydrogen peroxide and converting the starting titanium compound or titanium hydroxide into peroxotitanic acid, the reaction temperature is preferably set to from 5 to 80° C. and the reaction time is preferably set to from 30 minutes to 24 hours.

The resulting transition metal and tin-containing peroxotitanic acid solution may, for the sake of pH adjustment, etc., include an alkaline substance or an acidic substance. Illustrative examples of what are referred to here as alkaline substances include ammonia, sodium hydroxide and calcium hydroxide. Illustrative examples of acidic substances include inorganic acids such as sulfuric acid, nitric acid, hydrochloric acid, carbonic acid, phosphoric acid and hydrogen peroxide; and organic acids such as formic acid, citric acid, oxalic acid, lactic acid and glycolic acid. The pH of the transition metal and tin-containing peroxotitanic acid solution obtained at this time is from 1 to 9, with a pH of from 4 to 7 being preferred from the standpoint of safety during handling.

Step (2):

In Step (2), the transition metal and tin-containing peroxotitanic acid solution obtained in Step (1) is furnished to a hydrothermal reaction under pressure control and a temperature of from 80 to 250° C., preferably from 100 to 250° C., for 0.01 to 24 hours. From the standpoint of reaction efficiency and reaction controllability, a reaction temperature of from 80 to 250° C. is appropriate. As a result, the transition metal and tin-containing peroxotitanic acid is converted to transition metal and tin-containing titanium oxide fine particles. Here, "under pressure control" means to carry out suitable pressurization in such a way as to be able to maintain the reaction temperature in cases where the reaction temperature exceeds the boiling point of the dispersion medium. This includes control at atmospheric pressure in cases where the temperature is at or below the boiling point of the dispersion medium. The pressure used here is generally from about 0.12 MPa to about 4.5 MPa, preferably from about 0.15 MPa to about 4.5 MPa, and more preferably from about 0.20 MPa to about 4.5 MPa. The reaction time is preferably from 1 minute to 24 hours. Step (2) thus provides transition metal and tin-containing titanium oxide fine particles that serve as the first type of titanium oxide fine particle.

The particle size of the titanium oxide fine particles thus obtained is preferably in the range already mentioned above. It is possible to control the particle size by adjusting the reaction conditions. For example, the particle size can be made smaller by shortening the reaction time.

Step (3):

In Step (3), separate from above Steps (1) and (2), an iron group element-containing peroxotitanic acid solution is prepared by reacting a starting titanium compound, an iron group compound, a basic substance and hydrogen peroxide in an aqueous dispersion medium. Aside from using an iron group compound in place of the transition metal compound and the tin compound in Step (1), the reaction is carried out in exactly the same way.

That is, the starting materials, these being a starting titanium compound, an iron group compound, an aqueous dispersion medium, a basic substance and hydrogen peroxide, each of which has been described above, are used by being compounded in the foregoing manner, and then furnished to a reaction under the temperature and time conditions mentioned above.

The resulting iron group element-containing peroxotitanic acid solution may include also an alkaline substance or an acidic substance in order to, for example, adjust the pH. The alkaline substance and acidic substance, and pH adjustment as well, may be handled in the same way as described above.

Step (4):

In Step (4), the iron group element-containing peroxotitanic acid solution obtained in Step (3) is furnished to a hydrothermal reaction under pressure control and a temperature of from 80 to 250° C., preferably from 100 to 250° C., for 0.01 to 24 hours. From the standpoint of reaction efficiency and reaction controllability, a reaction temperature of from 80 to 250° C. is appropriate. As a result, the iron group element-containing peroxotitanic acid is converted to iron group element-containing titanium oxide fine particles. Here, "under pressure control" means to carry out suitable pressurization in such a way as to be able to maintain the reaction temperature in cases where the reaction temperature exceeds the boiling point of the dispersion medium. This includes control at atmospheric pressure in cases where the temperature is at or below the boiling point of the dispersion medium. The pressure used here is generally from about 0.12 MPa to about 4.5 MPa, preferably from about 0.15 MPa to about 4.5 MPa, and more preferably form about 0.20 MPa to about 4.5 MPa. The reaction time is preferably from 1 minute to 24 hours. Step (4) thus provides iron group element-containing titanium oxide fine particles that serve as the second type of titanium oxide fine particle.

The particle size of the titanium oxide fine particles thus obtained is preferably in the range already mentioned above. It is possible to control the particle size by adjusting the reaction conditions. For example, the particle size can be made smaller by shortening the reaction time.

Step (5):

In Step (5), the first titanium oxide fine particle dispersion obtained from Steps (1) and (2) and the second titanium oxide fine particle dispersion obtained from Steps (3) and (4) are mixed together. The mixing method is not particularly limited, and may include agitation with an agitator or dispersion with an ultrasonic disperser. The temperature at the time of mixture is preferably from 20 to 100° C., and the mixing time is preferably from 1 minute to 3 hours. As for the mixing ratio, mixing should be carried out such that the weight ratio between the titanium oxide fine particles in the respective titanium oxide fine particle dispersions becomes the weight ratio already described above.

The weight of the titanium oxide fine particles contained in the titanium oxide fine particle dispersion can be calculated from the amount and concentration of the titanium oxide fine particle dispersion. Using the following formula, the concentration can be calculated from the weight of the nonvolatile matter (titanium oxide fine particles) remaining when a portion of the titanium oxide fine particle dispersion is sampled and heated at 105° C. for 3 hours to evaporate the solvent and the weight of the sampled titanium oxide fine particle dispersion.

Concentration (%) of titanium oxide fine particle dispersion=Weight of nonvolatile matter (g)/Weight of titanium oxide fine particle dispersion (g)×100

As noted above, from the standpoint of the ease of producing photocatalytic thin films of the required thickness, the total concentration of the first type of titanium oxide fine particle and the second type of titanium oxide fine particle in the visible light-responsive photocatalytic titanium oxide fine particle dispersion thus produced is preferably from 0.01 to 20 wt %, and more preferably from 0.5 to 10 wt %. With regard to adjustment of the concentration, when the concentration is higher than the desired concentration, the concentration can be lowered by adding aqueous solvent to dilute the dispersion; when the concentration is lower than the desired concentration, the concentration can be increased by evaporating or filtering off some of the aqueous solvent. The concentration can be determined as described above.

In cases where the above-described film formability-increasing binder is added, such addition is preferably carried out to a visible light-responsive photocatalytic titanium oxide fine particle dispersion whose concentration has been adjusted as described above such that the desired concentration is achieved following mixture of the aqueous binder solution that is added.

<Member Having Photocatalytic Thin Film on Surface>

The visible light-responsive photocatalytic titanium oxide fine particle dispersion of the invention can be used to form a photocatalytic film on the surface of various types of members. No particular limitation is imposed here on the type of member. Examples of materials of which the member may be composed include organic materials and inorganic materials. Such members may have a variety of shapes according to their respective purposes and applications.

Illustrative examples of organic materials include synthetic resin materials such as vinyl chloride resins (PVC), polyethylene (PE), polypropylene (PP), polycarbonates (PC), acrylic resins, polyacetals, fluororesins, silicone resins, ethylene-vinyl acetate copolymers (EVA), acrylonitrile-butadiene rubbers (NBR), polyethylene terephthalate (PET), polyethylene naphthalate (PEN), polyvinyl butyral (PVB), ethylene-vinyl alcohol copolymers (EVOH), polyimide resins, polyphenylene sulfides (PPS), polyetherimides (PEI), polyetheretherimides (PEEI), polyetheretherketones (PEEK), melamine resins, phenolic resins and acrylonitrile-butadiene-styrene (ABS) resins; natural materials such as natural rubbers; and semi-synthetic materials made of the above synthetic resin materials and natural materials. These materials may be rendered into products of a required shape and construction, such as films, sheets, textile materials, textile products and other moldings or laminates.

Examples of inorganic materials include nonmetallic inorganic materials and metallic inorganic materials.

Examples of nonmetallic inorganic materials include glass, ceramic and stone. These may be rendered into products of various forms, such as tile, glass, mirrors, walls and decorative materials.

Examples of metallic inorganic materials include cast iron, steel, iron, ferrous alloys, aluminum, aluminum alloys, nickel, nickel alloys and diecast zinc. These may be plated with the above metallic inorganic materials or coated with the above organic materials, or may be platings applied to the surface of the above organic materials or nonmetallic inorganic materials.

Of the various above members, the visible light-responsive photocatalytic titanium oxide fine particle dispersion of the invention is especially useful for producing transparent photocatalytic thin films on PET and other polymer films.

The method of forming a photocatalytic film on the surface of various types of members may be one in which the visible light-responsive photocatalytic titanium oxide fine particle dispersion is coated onto the surface of the member by a known coating method such as spray coating or dip coating, and then dried by a known drying method such as far-infrared ray drying, drying by induction heating or hot-air drying. The thickness of the photocatalytic film may be variously selected, although a thickness in the range of from 10 nm to 10 µm is generally preferred.

The photocatalytic film formed in this way is transparent and provides not only good photocatalysis when exposed to light in the ultraviolet region (10 to 400 nm) as in the prior art, but also excellent photocatalysis even when exposed only to light in the visible region (400 to 800 nm) from which conventional photocatalysts have been unable to obtain sufficient photocatalysis. Owing to the photocatalysis of titanium oxide, various types of members on which this photocatalytic film has been formed decompose organic matter adsorbed to the surface, thus making it possible to exhibit effects such as cleaning, deodorizing and disinfection of the member surface.

EXAMPLES

The invention is illustrated more fully below by way of Examples and Comparative Examples, although these Examples are not intended to limit the invention. The various measurements in the invention were carried out as described below.

(1) Average Particle Size ($D_{50}$) of Titanium Oxide Fine Particles in Dispersion The average particle size ($D_{50}$) of titanium oxide fine particles in a dispersion were measured using a particle size analyzer (trade name: "Nanotrac UPA-EX150"; from Nikkiso Co., Ltd.).

(2) Test of Photocatalytic Thin-Film Performance in Decomposition of Acetaldehyde Gas (Under LED Irradiation)

The activity of a photocatalytic thin-film produced by coating and drying the dispersion was evaluated by means of decomposition reactions on acetaldehyde gas. Evaluation was carried out as follows by a batch-type method for evaluating gas decomposition performance.

An evaluation sample obtained by forming a photocatalytic thin film containing about 50 mg (dry weight) of photocatalytic fine particles over the entire surface of an A4-size (210 mm×297 mm) PET film was set within a 5 L capacity stainless steel cell having a quartz glass window, following which the cell was filled with 5 ppm concentration acetaldehyde gas that was moisture-conditioned to 50% humidity, and the sample was exposed to light at an illuminance of 30,000 Lx with an LED lamp (model number: TH-211×200SW, from CCS Inc.; spectral distribution, 400 to 800 nm) positioned at the top of the cell. When acetaldehyde gas decomposes on account of the photocatalyst on the thin film, the acetaldehyde gas concentration within the cell decreases. By measuring the concentration, it is possible to determine the amount of acetaldehyde gas that has decomposed. The acetaldehyde gas concentration was measured with a photoacoustic multigas monitor (trade name: INNOVA 1412, from LumaSense Technologies Inc.), and evaluation was carried out based on the following criteria by comparing the time that it took for the concentration of acetaldehyde gas to decrease to (1) 1 ppm and (2) 0.03 ppm from the initial concentration of 5 ppm. The test was performed for up to 20 hours.

Excellent (Exc): Decreases to reference value in 10 hours or less

Good: Decreases to reference value in 20 hours or less

Marginal: A decrease from initial concentration (5 ppm) is observable, but cannot decrease to reference values (1 ppm and 0.03 ppm) within 20 hours No Good (NG): No decrease from initial concentration (5 ppm) is observable (no decrease whatsoever)

(3) Identification of Crystal Phases of Titanium Oxide Fine Particles

The crystal phases of the titanium oxide fine particles were identified by powder x-ray diffraction analysis (a desktop x-ray powder diffractometer available under the trade name D2 PHASER from Bruker AXS) on the titanium oxide fine particle powders recovered by drying the resulting titanium oxide fine particle dispersions at 105° C. for 3 hours.

Example 1

<Preparation of Dispersion of Titanium Oxide Fine Particles Containing Tin and Molybdenum in Solid Solution>

A tin and molybdenum-containing titanium hydroxide precipitate was obtained by adding and dissolving tin(IV) chloride in a 36 wt % aqueous solution of titanium(IV) chloride to a molar ratio Ti/Sn of 20, diluting this ten-fold with pure water, and then gradually adding to this aqueous solution, 10 wt % ammonia water in which molybdenum (VI) oxide had been added and dissolved to a Ti/Mo (molar ratio) of 20 based on the titanium constituent in the aqueous solution of titanium(IV) chloride, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated tin and molybdenum-containing titanium hydroxide precipitate to a molar ratio $H_2O_2/(Ti+Sn+Mo)$ of 10, after which the system was stirred at 50° C. for three hours to fully carry out the reaction, thereby giving a clear, orange-colored tin and molybdenum-containing peroxotitanic acid solution (a).

A 500 mL autoclave was charged with 400 mL of the tin and molybdenum-containing peroxotitanic acid solution (a), and this was hydrothermally treated at 150° C. for 90 minutes. Next, the concentration was adjusted by adding pure water, thereby giving a dispersion (solids concentration, 1 wt %) of titanium oxide fine particles (A) containing tin and molybdenum in solid solution. Powder x-ray diffraction analysis was carried out on the titanium oxide fine particles (A), whereupon the only observed peaks were rutile-type titanium oxide peaks, indicating that the tin and molybdenum were in solid solution in the titanium oxide.

<Preparation of Dispersion of Titanium Oxide Fine Particles Containing Iron in Solid Solution>

An iron-containing titanium hydroxide precipitate was obtained by adding iron(III) chloride to a 36 wt % aqueous solution of titanium(IV) chloride to a molar ratio Ti/Fe of 10, diluting this ten-fold with pure water, and then gradually adding to the aqueous solution, 10 wt % ammonia water, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated iron-containing titanium hydroxide precipitate to a molar ratio $H_2O_2/(Ti+Fe)$ of 8, after which the system was stirred at 40° C. for two hours to fully carry out the reaction, thereby giving a clear, orange-colored iron-containing peroxotitanic acid solution (b).

A 500 mL autoclave was charged with 400 mL of the iron-containing peroxotitanic acid solution (b), and this was hydrothermally treated at 130° C. for 90 minutes. Next, the concentration was adjusted by adding pure water, thereby giving a dispersion (solids concentration, 1 wt %) of titanium oxide fine particles (B) containing iron in solid solution. Powder x-ray diffraction analysis was carried out on the titanium oxide fine particles (B), whereupon the only observed peaks were anatase-type titanium oxide peaks, indicating that the iron was in solid solution in the titanium oxide.

A visible light-responsive photocatalytic titanium oxide fine particle dispersion (E-1) according to the invention was obtained by mixing together the respective dispersions of titanium oxide fine particles (A) and titanium oxide fine particles (B) such that the weight ratio of the titanium oxide fine particles (A) to the titanium oxide fine particles (B), expressed as (A):(B), becomes 50:50.

A liquid coating for evaluation was produced by adding a silica-based binder (colloidal silica available under the trade name Snotex 20 from Nissan Chemical Industries, Ltd.; average particle size, 10 to 20 nm; an aqueous solution having a $SiO_2$ concentration of 20 wt %) to the photocatalytic titanium oxide fine particle dispersion (E-1) so as to give a weight ratio $TiO_2/SiO_2$ of 1.5.

The liquid coating for evaluation was coated onto an A4-size PET film with a #7 wire bar coater in such a way as to form a photocatalytic thin film (thickness, about 0.2 μm) containing 50 mg of photocatalytic titanium oxide fine particles and dried for one hour in an oven set to 80° C., thereby giving a sample member for evaluation of the acetaldehyde gas decomposition performance. The acetaldehyde gas decomposition performance by this photocatalytic thin film was measured using the batch-type gas decomposition performance evaluation method, whereupon the acetaldehyde gas concentration decreased to 1 ppm after 2.5 hours of LED (wavelength, 400 to 800 nm) irradiation (Excellent), and to 0.03 ppm after 6.1 hours of LED irradiation (Excellent).

Example 2

<Preparation of Dispersion of Titanium Oxide Fine Particles Containing Tin and Molybdenum in Solid Solution>

Aside from adding molybdenum(VI) oxide such that Ti/Mo (molar ratio) becomes 3.3 and setting the hydrothermal treatment time to 120 minutes, a dispersion of titanium oxide fine particles (C) containing tin and molybdenum in solid solution (solids concentration, 1 wt %) was obtained in the same way as in Example 1. Powder x-ray diffraction analysis was carried out on the titanium oxide fine particles (C), whereupon the only observed peaks were rutile-type titanium oxide peaks, indicating that the tin and molybdenum were in solid solution in the titanium oxide.

A visible light-responsive photocatalytic titanium oxide fine particle dispersion (E-2) according to the invention was obtained by mixing together the respective dispersions of titanium oxide fine particles (C) and titanium oxide fine particles (B) such that the weight ratio of the titanium oxide fine particles (C) to the titanium oxide fine particles (B), expressed as (C):(B), becomes 50:50.

A coating liquid for evaluation and a photocatalytic thin film were produced from the photocatalytic titanium oxide fine particle dispersion (E-2) in the same way as in Example 1. The acetaldehyde gas decomposition performance was measured, whereupon the acetaldehyde gas concentration decreased to 1 ppm after 2.3 hours of LED irradiation (Excellent), and to 0.03 ppm after 4.1 hours of LED irradiation (Excellent).

Example 3

<Preparation of Dispersion of Titanium Oxide Fine Particles Containing Tin and Molybdenum in Solid Solution>

Aside from adding molybdenum(VI) oxide such that Ti/Mo (molar ratio) becomes 100, a dispersion of titanium oxide fine particles (D) containing tin and molybdenum in solid solution (solids concentration, 1 wt %) was obtained in the same way as in Example 1. Powder x-ray diffraction analysis was carried out on the titanium oxide fine particles (D), whereupon the only observed peaks were rutile-type titanium oxide peaks, indicating that the tin and molybdenum were in solid solution in the titanium oxide.

A visible light-responsive photocatalytic titanium oxide fine particle dispersion (E-3) according to the invention was obtained by mixing together the respective dispersions of titanium oxide fine particles (D) and titanium oxide fine particles (B) such that the weight ratio of the titanium oxide fine particles (D) to the titanium oxide fine particles (B), expressed as (D):(B), becomes 50:50.

A coating liquid for evaluation and a photocatalytic thin film were produced from the photocatalytic titanium oxide fine particle dispersion (E-3) in the same way as in Example 1. The acetaldehyde gas decomposition performance was measured, whereupon the acetaldehyde gas concentration decreased to 1 ppm after 10.4 hours of LED irradiation (Good), and to 0.03 ppm after 19.0 hours of LED irradiation (Good).

Example 4

<Preparation of Dispersion of Titanium Oxide Fine Particles Containing Tin and Molybdenum in Solid Solution>

Aside from adding an aqueous solution of titanium(IV) oxide such that Ti/Sn (molar ratio) becomes 5 and setting the hydrothermal treatment temperature to 180° C., a dispersion of titanium oxide fine particles (E) containing tin and molybdenum in solid solution (solids concentration, 1 wt %) was obtained in the same way as in Example 1. Powder x-ray diffraction analysis was carried out on the titanium oxide fine particles (E), whereupon the only observed peaks were rutile-type titanium oxide peaks, indicating that the tin and molybdenum were in solid solution in the titanium oxide.

A visible light-responsive photocatalytic titanium oxide fine particle dispersion (E-4) according to the invention was obtained by mixing together the respective dispersions of titanium oxide fine particles (E) and titanium oxide fine particles (B) such that the weight ratio of the titanium oxide fine particles (E) to the titanium oxide fine particles (B), expressed as (E):(B), becomes 50:50.

A coating liquid for evaluation and a photocatalytic thin film were produced from the photocatalytic titanium oxide fine particle dispersion (E-4) in the same way as in Example 1. The acetaldehyde gas decomposition performance was measured, whereupon the acetaldehyde gas concentration decreased to 1 ppm after 4.1 hours of LED irradiation (Excellent), and to 0.03 ppm after 7.6 hours of LED irradiation (Excellent).

Example 5

<Preparation of Dispersion of Titanium Oxide Fine Particles Containing Tin and Molybdenum in Solid Solution>

Aside from adding an aqueous solution of titanium(IV) oxide such that Ti/Sn (molar ratio) becomes 33 and setting the hydrothermal treatment temperature to 140° C., a dispersion of titanium oxide fine particles (F) containing tin and molybdenum in solid solution (solids concentration, 1 wt %) was obtained in the same way as in Example 1. Powder x-ray diffraction analysis was carried out on the titanium oxide fine particles (F), whereupon the only observed peaks were anatase-type titanium oxide peaks and rutile-type titanium oxide peaks, indicating that the tin and molybdenum were in solid solution in the titanium oxide.

A visible light-responsive photocatalytic titanium oxide fine particle dispersion (E-5) according to the invention was obtained by mixing together the respective dispersions of titanium oxide fine particles (F) and titanium oxide fine particles (B) such that the weight ratio of the titanium oxide fine particles (F) to the titanium oxide fine particles (B), expressed as (F):(B), becomes 50:50.

A coating liquid for evaluation and a photocatalytic thin film were produced from the photocatalytic titanium oxide fine particle dispersion (E-5) in the same way as in Example 1. The acetaldehyde gas decomposition performance was measured, whereupon the acetaldehyde gas concentration decreased to 1 ppm after 7.5 hours of LED irradiation (Excellent), and to 0.03 ppm after 12.5 hours of LED irradiation (Good).

Example 6

<Preparation of Dispersion of Titanium Oxide Fine Particles Containing Tin and Molybdenum in Solid Solution>

Aside from adding molybdenum(VI) oxide such that Ti/Mo (molar ratio) becomes 12.5, a dispersion of titanium oxide fine particles (G) containing tin and molybdenum in solid solution (solids concentration, 1 wt %) was obtained in the same way as in Example 1. Powder x-ray diffraction analysis was carried out on the titanium oxide fine particles (G), whereupon the only observed peaks were rutile-type titanium oxide peaks, indicating that the tin and molybdenum were in solid solution in the titanium oxide.

<Preparation of Dispersion of Titanium Oxide Fine Particles Containing Iron in Solid Solution>

Aside from adding iron(III) chloride such that Ti/Fe (molar ratio) becomes 20 and setting the hydrothermal treatment time to 120 minutes, a dispersion of titanium oxide fine particles (H) containing iron in solid solution (solids concentration, 1 wt %) was obtained in the same way as in Example 1. Powder x-ray diffraction analysis was carried out on the titanium oxide fine particles (H), whereupon the only observed peaks were anatase-type titanium oxide peaks, indicating that the iron was in solid solution in the titanium oxide.

A visible light-responsive photocatalytic titanium oxide fine particle dispersion (E-6) according to the invention was obtained by mixing together the respective dispersions of titanium oxide fine particles (G) and titanium oxide fine particles (H) such that the weight ratio of the titanium oxide fine particles (G) to the titanium oxide fine particles (H), expressed as (G):(H), becomes 90:10.

A coating liquid for evaluation and a photocatalytic thin film were produced from the photocatalytic titanium oxide fine particle dispersion (E-6) in the same way as in Example 1. The acetaldehyde gas decomposition performance was measured, whereupon the acetaldehyde gas concentration decreased to 1 ppm after 8.8 hours of LED irradiation (Excellent), and to 0.03 ppm after 19.8 hours of LED irradiation (Good).

Example 7

A visible light-responsive photocatalytic titanium oxide fine particle dispersion (E-7) according to the invention was obtained by mixing together the respective dispersions of titanium oxide fine particles (G) and titanium oxide fine particles (H) such that the weight ratio of the titanium oxide fine particles (G) to the titanium oxide fine particles (H), expressed as (G):(H), becomes 60:40.

A coating liquid for evaluation and a photocatalytic thin film were produced from the photocatalytic titanium oxide fine particle dispersion (E-7) in the same way as in Example 1. The acetaldehyde gas decomposition performance was measured, whereupon the acetaldehyde gas concentration decreased to 1 ppm after 2.4 hours of LED irradiation (Excellent), and to 0.03 ppm after 7.8 hours of LED irradiation (Excellent).

Example 8

A visible light-responsive photocatalytic titanium oxide fine particle dispersion (E-8) according to the invention was obtained by mixing together the respective dispersions of titanium oxide fine particles (A) and titanium oxide fine particles (H) such that the weight ratio of the titanium oxide fine particles (A) to the titanium oxide fine particles (H), expressed as (A):(H), becomes 50:50.

A coating liquid for evaluation and a photocatalytic thin film were produced from the photocatalytic titanium oxide fine particle dispersion (E-8) in the same way as in Example 1. The acetaldehyde gas decomposition performance was measured, whereupon the acetaldehyde gas concentration decreased to 1 ppm after 6.3 hours of LED irradiation (Excellent), and to 0.03 ppm after 15.3 hours of LED irradiation (Good).

Example 9

<Preparation of Dispersion of Titanium Oxide Fine Particles Containing Tin and Vanadium in Solid Solution>

A tin and vanadium-containing titanium hydroxide precipitate was obtained by adding and dissolving, in a 36 wt % aqueous solution of titanium(IV) chloride: tin(IV) chloride to a molar ratio Ti/Sn of 20 and vanadyl(IV) sulfate to a molar ratio Ti/V of 2,000, diluting this ten-fold with pure water and then gradually adding 10 wt % ammonia water, thereby effecting neutralization and hydrolysis. The pH of the solution at this time was 8.5. The resulting precipitate was deionization treated by the repeated addition of pure water and decantation. Next, 35 wt % hydrogen peroxide water was added to the deionization-treated tin and vanadium-containing titanium hydroxide precipitate to a molar ratio $H_2O_2/(Ti+Sn+V)$ of 10, after which the system was stirred at 50° C. for three hours to fully carry out the reaction, thereby giving a clear, orange-colored tin and vanadium-containing peroxotitanic acid solution (i).

A 500 mL autoclave was charged with 400 mL of the tin and vanadium-containing peroxotitanic acid solution (i), and this was hydrothermally treated at 150° C. for 90 minutes. Next, the concentration was adjusted by adding pure water, thereby giving a dispersion of titanium oxide fine particles (I) containing tin and vanadium in solid solution (solids concentration, 1 wt %). Powder x-ray diffraction analysis was carried out on the titanium oxide fine particles (I), whereupon the only observed peaks were rutile-type titanium oxide peaks, indicating that the tin and vanadium were in solid solution in the titanium oxide.

A visible light-responsive photocatalytic titanium oxide fine particle dispersion (E-9) according to the invention was obtained by mixing together the respective dispersions of titanium oxide fine particles (I) and titanium oxide fine particles (B) such that the weight ratio of the titanium oxide fine particles (I) to the titanium oxide fine particles (B), expressed as (I):(B), becomes 50:50.

A coating liquid for evaluation and a photocatalytic thin film were produced from the photocatalytic titanium oxide fine particle dispersion (E-9) in the same way as in Example 1. The acetaldehyde gas decomposition performance was measured, whereupon the acetaldehyde gas concentration decreased to 1 ppm after 6.5 hours of LED irradiation (Excellent), and to 0.03 ppm after 13.8 hours of LED irradiation (Good).

Example 10

<Preparation of Dispersion of Titanium Oxide Fine Particles Containing Tin and Vanadium in Solid Solution>

Aside from adding vanadyl(IV) sulfate such that Ti/V (molar ratio) becomes 500 and setting the hydrothermal treatment temperature to 180° C. and the hydrothermal treatment time to 20 minutes, a dispersion of titanium oxide fine particles (J) containing tin and vanadium in solid solution (solids concentration, 1 wt %) was obtained in the same way as in Example 9. Powder x-ray diffraction analysis was carried out on the titanium oxide fine particles (J), whereupon the only observed peaks were rutile-type titanium oxide peaks, indicating that the tin and vanadium were in solid solution in the titanium oxide.

A visible light-responsive photocatalytic titanium oxide fine particle dispersion (E-10) according to the invention was obtained by mixing together the respective dispersions of titanium oxide fine particles (J) and titanium oxide fine particles (H) such that the weight ratio of the titanium oxide fine particles (J) to the titanium oxide fine particles (H), expressed as (J):(H), becomes 50:50.

A coating liquid for evaluation and a photocatalytic thin film were produced from the photocatalytic titanium oxide fine particle dispersion (E-10) in the same way as in Example 1. The acetaldehyde gas decomposition performance was measured, whereupon the acetaldehyde gas concentration decreased to 1 ppm after 7.2 hours of LED irradiation (Excellent), and to 0.03 ppm after 14.6 hours of LED irradiation (Good).

Example 11

A visible light-responsive photocatalytic titanium oxide fine particle dispersion (E-11) according to the invention was obtained by mixing together the respective dispersions of titanium oxide fine particles (A), titanium oxide fine particles (I) and titanium oxide fine particles (B) such that the weight ratio among the titanium oxide fine particles (A), the titanium oxide fine particles (I) and the titanium oxide fine particles (B), expressed as (A): (I):(B), becomes 25:25:50.

A coating liquid for evaluation and a photocatalytic thin film were produced from the photocatalytic titanium oxide fine particle dispersion (E-11) in the same way as in Example 1. The acetaldehyde gas decomposition performance was measured, whereupon the acetaldehyde gas concentration decreased to 1 ppm after 2.0 hours of LED irradiation (Excellent), and to 0.03 ppm after 3.5 hours of LED irradiation (Excellent).

Comparative Example 1

A titanium oxide fine particle dispersion (C-1) was obtained using only a dispersion of titanium oxide fine particles (A).

A coating liquid for evaluation and a photocatalytic thin film were produced from the photocatalytic titanium oxide fine particle dispersion (C-1) in the same way as in Example 1. The acetaldehyde gas decomposition performance was measured, whereupon the acetaldehyde gas concentration decreased to 3.7 ppm after 20 hours of LED irradiation (Marginal).

Comparative Example 2

A titanium oxide fine particle dispersion (C-2) was obtained using only a dispersion of titanium oxide fine particles (B).

A coating liquid for evaluation and a photocatalytic thin film were produced from the photocatalytic titanium oxide fine particle dispersion (C-2) in the same way as in Example 1. The acetaldehyde gas decomposition performance was measured, whereupon a decrease in the acetaldehyde gas concentration was not observed even after 20 hours of LED irradiation (No Good).

Comparative Example 3

<Preparation of Dispersion of Titanium Oxide Fine Particles Containing Copper in Solid Solution>

A copper-containing titanium hydroxide precipitate was obtained by adding and dissolving copper(II) chloride in a 36 wt % aqueous solution of titanium(IV) chloride to a molar ratio Ti/Cu of 20, diluting this ten-fold with pure water and then gradually adding 10 wt % ammonia water, thereby effecting neutralization and hydrolysis. The pH of the solution at this time was 7.5. The resulting precipitate was deionization treated by the repeated addition of pure water and decantation. Next, 35 wt % hydrogen peroxide water was added to the deionization-treated copper-containing titanium hydroxide precipitate to a molar ratio $H_2O_2/(Ti+Cu)$ of 12, after which the system was stirred at 40° C. for three hours to fully carry out the reaction, thereby giving a clear, green-colored copper-containing peroxotitanic acid solution (k).

A 500 mL autoclave was charged with 400 mL of the copper-containing peroxotitanic acid solution (k), and this was hydrothermally treated at 130° C. for 90 minutes. Next, the concentration was adjusted by adding pure water, thereby giving a dispersion of titanium oxide fine particles (K) containing copper in solid solution (solids concentration, 1 wt %). Powder x-ray diffraction analysis was carried out, whereupon the only observed peaks were anatase-type titanium oxide peaks, indicating that the copper was in solid solution in the titanium oxide.

A titanium oxide fine particle dispersion (C-3) was obtained using only a dispersion of titanium oxide fine particles (K).

A coating liquid for evaluation and a photocatalytic thin film were produced from the photocatalytic titanium oxide fine particle dispersion (C-3) in the same way as in Example 1. The acetaldehyde gas decomposition performance was measured, whereupon the acetaldehyde gas concentration decreased to 3.2 ppm after 20 hours of LED irradiation (Marginal).

Comparative Example 4

A titanium oxide fine particle dispersion (C-4) was obtained by mixing together the respective dispersions of titanium oxide fine particles (G) and titanium oxide fine particles (K) such that the weight ratio of the titanium oxide fine particles (G) to the titanium oxide fine particles (K), expressed as (G):(K), becomes 90:10.

A coating liquid for evaluation and a photocatalytic thin film were produced from the titanium oxide fine particle dispersion (C-4) in the same way as in Example 1. The acetaldehyde gas decomposition performance was measured, whereupon the acetaldehyde gas concentration decreased to 1 ppm after 2.0 hours of LED irradiation (Excellent), but the acetaldehyde gas concentration only decreased to 0.16 ppm after 20 hours of LED irradiation (Marginal).

Comparative Example 5

A titanium oxide fine particle dispersion (C-5) was obtained by mixing together the respective dispersions of titanium oxide fine particles (G) and titanium oxide fine particles (K) such that the weight ratio of the titanium oxide fine particles (G) to the titanium oxide fine particles (K), expressed as (G):(K), becomes 60:40.

A coating liquid for evaluation and a photocatalytic thin film were produced from the titanium oxide fine particle dispersion (C-5) in the same way as in Example 1. The acetaldehyde gas decomposition performance was measured, whereupon the acetaldehyde gas concentration decreased to 1 ppm after 6.8 hours of LED irradiation (Excellent), but the acetaldehyde gas concentration only decreased to 0.20 ppm after 20 hours of LED irradiation (Marginal).

Comparative Example 6

A titanium oxide fine particle dispersion (C-6) was obtained by mixing together the respective dispersions of titanium oxide fine particles (I) and titanium oxide fine particles (K) such that the weight ratio of the titanium oxide fine particles (I) to the titanium oxide fine particles (K), expressed as (I):(K), becomes 50:50.

A coating liquid for evaluation and a photocatalytic thin film were produced from the titanium oxide fine particle dispersion (C-6) in the same way as in Example 1. The acetaldehyde gas decomposition performance was measured, whereupon the acetaldehyde gas concentration decreased to 1 ppm after 6.0 hours of LED irradiation (Excellent), but the acetaldehyde gas concentration only decreased to 0.13 ppm after 20 hours of LED irradiation (Marginal).

Comparative Example 7

<Preparation of Dispersion of Titanium Oxide Fine Particles Containing Tin in Solid Solution>

A tin-containing titanium hydroxide precipitate was obtained by adding and dissolving tin(IV) chloride in a 36 wt % aqueous solution of titanium(IV) chloride to a molar ratio Ti/Sn of 20, diluting this ten-fold with pure water and then gradually adding 10 wt % ammonia water, thereby effecting neutralization and hydrolysis. The pH of the solution at this time was 9. The resulting precipitate was deionization treated by the repeated addition of pure water and decantation. Next, 35 wt % hydrogen peroxide water was added to the deionization-treated tin-containing titanium hydroxide precipitate to a molar ratio $H_2O_2/(Ti+Sn)$ of 6, after which the system was stirred for one full day at room temperature to fully carry out the reaction, thereby giving a clear, orange-colored tin-containing peroxotitanic acid solution (1).

A 500 mL autoclave was charged with 400 mL of the tin-containing peroxotitanic acid solution (1), and this was hydrothermally treated at 150° C. for 90 minutes. Next, the concentration was adjusted by adding pure water, thereby giving a dispersion of titanium oxide fine particles (L) containing tin in solid solution (solids concentration, 1 wt %). Powder x-ray diffraction analysis was carried out on the titanium oxide fine particles (L), whereupon the only observed peaks were rutile-type titanium oxide peaks, indicating that the tin was in solid solution in the titanium oxide.

A titanium oxide fine particle dispersion (C-7) was obtained by mixing together the respective dispersions of titanium oxide fine particles (L) and titanium oxide fine particles (B) such that the weight ratio of the titanium oxide fine particles (L) to the titanium oxide fine particles (B), expressed as (L):(B), becomes 50:50.

A coating liquid for evaluation and a photocatalytic thin film were produced from the titanium oxide fine particle dispersion (C-7) in the same way as in Example 1. The acetaldehyde gas decomposition performance was measured, whereupon the acetaldehyde gas concentration decreased to 1 ppm after 18.6 hours of LED irradiation (Good), but the acetaldehyde gas concentration only decreased to 0.80 ppm after 20 hours of LED irradiation (Marginal).

Comparative Example 8

<Preparation of Dispersion of Titanium Oxide Fine Particles Containing Molybdenum in Solid Solution>

A molybdenum-containing titanium hydroxide precipitate was obtained by diluting a 36 wt % aqueous solution of titanium(IV) chloride ten-fold with pure water, adding and dissolving molybdenum(VI) oxide in this aqueous solution to a molar ratio Ti/Mo of 20 with respect to the titanium constituent in the aqueous solution of titanium (IV) chloride, and then gradually adding 10 wt % ammonia water, thereby effecting neutralization and hydrolysis. The pH of the solution at this time was 8. The resulting precipitate was deionization treated by the repeated addition of pure water and decantation. Next, 35 wt % hydrogen peroxide water was added to the deionization-treated molybdenum-containing titanium hydroxide precipitate to a molar ratio $H_2O_2/$(Ti+Mo) of 8, after which the system was stirred for one full day at room temperature to fully carry out the reaction, thereby giving a clear, orange-colored molybdenum-containing peroxotitanic acid solution (m).

A 500 mL autoclave was charged with 400 mL of the molybdenum-containing peroxotitanic acid solution (m), and this was hydrothermally treated at 130° C. for 120 minutes. Next, the concentration was adjusted by adding pure water, thereby giving a dispersion of titanium oxide fine particles (M) containing molybdenum in solid solution (solids concentration, 1 wt %). Powder x-ray diffraction analysis was carried out on the titanium oxide fine particles (M), whereupon the only observed peaks were anatase-type titanium oxide peaks, indicating that the molybdenum was in solid solution in the titanium oxide.

A titanium oxide fine particle dispersion (C-8) was obtained by mixing together the respective dispersions of titanium oxide fine particles (M) and titanium oxide fine particles (B) such that the weight ratio of the titanium oxide fine particles (M) to the titanium oxide fine particles (B), expressed as (M):(B), becomes 50:50.

A coating liquid for evaluation and a photocatalytic thin film were produced from the photocatalytic titanium oxide fine particle dispersion (C-8) in the same way as in Example 1. The acetaldehyde gas decomposition performance was measured, whereupon the acetaldehyde gas concentration decreased to 4.1 ppm after 20 hours of LED irradiation (Marginal).

Comparative Example 9

<Preparation of Titanium Oxide Fine Particle Dispersion>

A titanium hydroxide precipitate was obtained by diluting a 36 wt % aqueous solution of titanium(IV) chloride ten-fold with pure water and then gradually adding 10 wt % ammonia water, thereby effecting neutralization and hydrolysis. The pH of the solution at this time was 9. The resulting precipitate was deionization treated by the repeated addition of pure water and decantation. Next, 35 wt % hydrogen peroxide water was added to the deionization-treated titanium hydroxide precipitate to a molar ratio $H_2O_2/Ti$ of 5, after which the system was stirred for one full day at room temperature to fully carry out the reaction, thereby giving a clear, yellow-colored peroxotitanic acid solution (n).

A 500 mL autoclave was charged with 400 mL of the peroxotitanic acid solution (n), and this was hydrothermally treated at 130° C. for 90 minutes. Next, the concentration was adjusted by adding pure water, thereby giving a dispersion of titanium oxide fine particles (N) (solids concentration, 1 wt %). Powder x-ray diffraction analysis was carried out on the titanium oxide fine particles (N), whereupon anatase-type titanium oxide peaks were observed.

A titanium oxide fine particle dispersion (C-9) was obtained using only the dispersion of titanium oxide fine particles (N).

A coating liquid for evaluation and a photocatalytic thin film were produced from the photocatalytic titanium oxide fine particle dispersion (C-9) in the same way as in Example 1. The acetaldehyde gas decomposition performance was measured, whereupon a decrease in the acetaldehyde gas concentration was not observed even after 20 hours of LED irradiation (No Good).

Comparative Example 11

<Recovery of Dissolved Constituent from Dispersion of Titanium Oxide Fine Particles Containing Iron in Solid Solution>

The dispersion of titanium oxide fine particles (B) containing iron in solid solution was centrifugally separated at 210,000×g with a small ultracentrifuge (available under the trade name Himac CS150NX from Hitachi Koki Co., Ltd.) into titanium oxide fine particles (B) containing iron in solid solution, solvent and dissolved constituent. The concentration of dissolved iron constituent in the solvent, as measured with an inductively coupled plasma (ICP) emission spectrometer (available under the trade name ICP Emission Spectrometer IRIS 1000 from Thermo Fisher Scientific), was 2.2 ppm, indicating that substantially all of the iron constituent added had entered into solid solution in the titanium oxide fine particles and was insoluble matter.

A titanium oxide fine particle dispersion (C-10) was obtained by mixing together the dispersion of titanium oxide fine particles (A) with the solvent and dissolved constituent from the dispersion of titanium oxide fine particles (B) such that the weight ratio between the titanium oxide fine particles (A) and the solvent and dissolved constituent obtained by separating off the titanium oxide fine particles (B) from the dispersion of titanium oxide fine particles (B) with an ultracentrifuge, expressed as (A):(B dissolved constituent), becomes 50:50.

A coating liquid for evaluation and a photocatalytic thin film were produced from the photocatalytic titanium oxide fine particle dispersion (C-10) in the same way as in Example 1. The acetaldehyde gas decomposition performance was measured, whereupon the acetaldehyde gas concentration decreased to 4.0 ppm after 20 hours of LED irradiation (Marginal).

Comparative Example 11

<Preparation of Dispersion of Titanium Oxide Fine Particles Having Iron Constituent Adsorbed to (Supported on) Surface>

A dispersion (C-11) of titanium oxide fine particles having an iron constituent adsorbed to the surface was obtained by mixing together a dispersion of titanium oxide fine particles (G) and an aqueous solution of iron(III) chloride dissolved in pure water such that the weight ratio between the titanium oxide fine particles (G) and the iron becomes 100:0.05.

A coating liquid for evaluation and a photocatalytic thin film were produced from the titanium oxide fine particle dispersion (C-11) in the same way as in Example 1. The acetaldehyde gas decomposition performance was measured, whereupon the acetaldehyde gas concentration decreased to 1 ppm after 4.6 hours of LED irradiation (Excellent), but the acetaldehyde gas concentration only decreased to 0.09 ppm after 20 hours of LED irradiation (Marginal).

Comparative Example 12

<Preparation of Dispersion of Titanium Oxide Fine Particles Having Iron Constituent Adsorbed to (Supported on) Surface>

A dispersion of titanium oxide fine particles (G) and an aqueous solution of iron(III) chloride obtained by dissolving iron(III) chloride in pure water were mixed together such that the weight ratio of the titanium oxide fine particles (G) to the iron becomes 100:0.5, whereupon the agglomeration and precipitation of titanium oxide fine particles in the dispersion (C-12) occurred, and so the evaluation was stopped. A method in which an iron group compound is added in this way to a dispersion worsens the dispersed state of the titanium oxide fine particles within the dispersion, greatly limiting the amount that can be added. In addition, the stability of the liquid also worsens.

Table 1 collectively presents the starting material ratios, hydrothermal treatment conditions and average particle sizes ($D_{50}$) for the titanium oxide fine particles used in Examples 1 to 11 and Comparative Examples 1 to 12.

TABLE 1

| Titanium oxide fine particle dispersion | Starting materials (molar ratio) | | | | | Hydrothermal treatment | | Average particle size (nm) |
|---|---|---|---|---|---|---|---|---|
| | Ti/Sn | Ti/Mo | Ti/V | Ti/Fe | Ti/Cu | Temperature (° C.) | Time (min) | |
| (A) | 20 | 20 | — | — | — | 150 | 90 | 12 |
| (B) | — | — | — | 10 | — | 130 | 90 | 18 |
| (C) | 20 | 3.3 | — | — | — | 150 | 120 | 10 |
| (D) | 20 | 100 | — | — | — | 150 | 90 | 9 |
| (E) | 5 | 20 | — | — | — | 180 | 90 | 9 |
| (F) | 33 | 20 | — | — | — | 140 | 90 | 15 |
| (G) | 20 | 12.5 | — | — | — | 150 | 90 | 10 |
| (H) | — | — | — | 20 | — | 130 | 120 | 16 |
| (I) | 20 | — | 2,000 | — | — | 150 | 90 | 9 |
| (J) | 20 | — | 500 | — | — | 180 | 20 | 7 |
| (K) | — | — | — | — | 20 | 130 | 90 | 18 |
| (L) | 20 | — | — | — | — | 150 | 90 | 10 |
| (M) | — | 20 | — | — | — | 130 | 120 | 16 |
| (N) | — | — | — | — | — | 130 | 90 | 20 |

Table 2 collectively presents the mixing ratios, average particles sizes, and acetaldehyde gas decomposition test results for the visible light-responsive photocatalytic fine particle dispersions in Examples 1 to 11 and Comparative Examples 1 to 12.

TABLE 2

| | | Evaluation sample | Titanium oxide dispersion | | Mixing ratio | Average particle size nm | 80% reduction (down to 1 ppm) hours | Rating | 99.4% reduction (down to 0.03 ppm) hours | Rating |
|---|---|---|---|---|---|---|---|---|---|---|
| | | | Type | | | | | | | |
| Example | 1 | E-1 | (A) | (B) | 50:50 | 15 | 2.5 | Exc | 6.1 | Exc |
| | 2 | E-2 | (C) | (B) | 50:50 | 11 | 2.3 | Exc | 4.1 | Exc |
| | 3 | E-3 | (D) | (B) | 50:50 | 14 | 10.4 | Good | 19.0 | Good |
| | 4 | E-4 | (E) | (B) | 50:50 | 15 | 4.1 | Exc | 7.6 | Exc |
| | 5 | E-5 | (F) | (B) | 50:50 | 17 | 7.5 | Exc | 12.5 | Good |
| | 6 | E-6 | (G) | (H) | 90:10 | 12 | 8.8 | Exc | 19.8 | Good |
| | 7 | E-7 | (G) | (H) | 60:40 | 12 | 2.4 | Exc | 7.8 | Exc |
| | 8 | E-8 | (A) | (H) | 50:50 | 15 | 6.3 | Exc | 15.3 | Good |
| | 9 | E-9 | (I) | (B) | 50:50 | 14 | 6.5 | Exc | 13.8 | Good |
| | 10 | E-10 | (J) | (H) | 50:50 | 10 | 7.2 | Exc | 14.6 | Good |
| | 11 | E-11 | (A), (I) | (B) | 25:25:50 | 14 | 2.0 | Exc | 3.5 | Exc |
| Comparative Example | 1 | C-1 | (A) | — | 100:0 | 12 | 3.7 ppm in 20 hrs | Marginal | — | NG |
| | 2 | C-2 | — | (B) | 0:100 | 18 | did not dissolve | NG | — | NG |
| | 3 | C-3 | — | (K) | 0:100 | 18 | 3.2 ppm in 20 hrs | Marginal | — | NG |
| | 4 | C-4 | (G) | (K) | 90:10 | 16 | 2.0 | Exc | 0.16 ppm in 20 hrs | Marginal |
| | 5 | C-5 | (G) | (K) | 60:40 | 16 | 6.8 | Exc | 0.20 ppm in 20 hrs | Marginal |
| | 6 | C-6 | (I) | (K) | 50:50 | 15 | 6.0 | Exc | 0.13 ppm in 20 hrs | Marginal |

TABLE 2-continued

| | Evaluation sample | | Titanium oxide dispersion | | Evaluation results | | | | |
|---|---|---|---|---|---|---|---|---|---|
| | | | Type | Mixing ratio | Average particle size nm | 80% reduction (down to 1 ppm) hours | Rating | 99.4% reduction (down to 0.03 ppm) hours | Rating |
| 7 | C-7 | (L) | (B) | 50:50 | 15 | 18.6 | Good | 0.80 ppm in 20 hrs | Marginal |
| 8 | C-8 | (M) | (B) | 50:50 | 18 | 4.1 ppm in 20 hrs | Marginal | — | NG |
| 9 | C-9 | (N) | — | 100:0 | 20 | did not dissolve | NG | — | NG |
| 10 | C-10 | (A) | (B) dissolved constituents | 50:50 | 12 | 4.0 ppm in 20 hrs | Marginal | — | NG |
| 11 | C-11 | (G) | iron chloride solution (aq) | 0.05 wt % (based on TiO$_2$) | 23 | 4.6 | Exc | 0.09 ppm in 20 hrs | Marginal |
| 12 | C-12 | (G) | iron chloride solution (aq) | 0.5 wt % (based on TiO$_2$) | — | Evaluation was stopped because dispersion incurred agglomeration and precipitation | | | |

As is apparent from the results in Examples 1 to 11, by mixing together a first type of titanium oxide fine particle containing in solid solution a tin constituent and a transition metal constituent that increases visible light responsiveness (a molybdenum constituent and/or a vanadium constituent) and a second type of titanium oxide fine particle containing in solid solution an iron constituent, the acetaldehyde gas decomposition is good even under irradiation with an LED lamp that emits only light in the visible region. Moreover, the acetaldehyde gas concentration can be lowered within an effective time period such as 20 hours or less, preferably 10 hours or less, and more preferably 5 hours or less, to the level of 0.03 ppm which is the indoor concentration guideline value for a chemical substance (acetaldehyde) within indoor air established by the Japanese Ministry of Health, Labor and Welfare.

As is apparent from the results in Comparative Examples 1 and 2, a sufficient photocatalytic activity under visible light irradiation cannot be obtained with either the first type of titanium oxide fine particle or the second type of titanium oxide fine particle alone.

As is apparent from the results in Comparative Examples 4, 5 and 6, when copper instead of iron is selected as the metal that is included in solid solution within the second type of titanium oxide fine particle, acetaldehyde gas decomposition under visible light irradiation is good at first when the acetaldehyde gas concentration is high, but a sufficient photocatalytic activity is not obtained on low-concentration acetaldehyde gas. By contrast, as demonstrated in each of the Examples, when iron was selected as the metal that is included in solid solution within the second type of titanium oxide fine particle, good activity was obtained even when the acetaldehyde gas concentration was low; indeed, the results obtained in the Examples showed that the acetaldehyde gas concentration can be lowered to 0.03 ppm or less.

As is apparent from the results in Comparative Examples 7 and 8, when the metal included in solid solution within the first type of titanium oxide fine particle is only tin or only a transition metal, a sufficient photocatalytic activity is not obtained under visible light irradiation. Therefore, in order to obtain a high activity under visible light irradiation, it is necessary to add to the first type of titanium oxide fine particle both tin and a transition metal constituent that increases the visible light responsiveness.

As is apparent from the results in Comparative Examples 3 and 9, when titanium oxide fine particles that contain iron in solid solution or titanium oxide fine particles that do not contain dissimilar metals in solid solution are used alone, no activity is obtained whatsoever under visible light irradiation. This is behavior that differs from titanium oxide particles that contain copper in solid solution.

As is apparent from the results in Comparative Example 10, the second type of titanium oxide fine particle is essential for increasing the visible light activity, and an iron constituent which is dissolved in the dispersion rather than being in solid solution within the second type of titanium oxide fine particle makes no contribution to increased activity. That is, the chief factor in the visible light activity-increasing effect is not iron constituent that leaks out of the second type of titanium oxide fine particle; rather, it depends on the combination of the second type of titanium oxide fine particle containing iron in solid solution with the first type of titanium oxide fine particle containing in solid solution tin and a transition metal constituent which increases the visible light responsiveness.

Moreover, as is apparent from the results in Comparative Examples 11 and 12, although dissolved iron constituent does contribute somewhat to increased visible light activity, a sufficient visible light activity on low-concentration acetaldehyde gas is not obtained. Also, when dissolved iron constituent is added in a large amount, this may cause the titanium oxide fine particles within the dispersion to agglomerate and precipitate out.

INDUSTRIAL APPLICABILITY

The visible light-responsive photocatalytic fine particle dispersions of the invention are useful for producing photocatalytic thin films by application to various types of substrates made of inorganic materials such as glass or metal or made of organic materials such as polymer films (e.g., PET films), and are particularly useful for producing clear photocatalytic thin films on polymer films.

The invention claimed is:

1. A visible light-responsive photocatalytic titanium oxide fine particle dispersion comprising two types of titanium oxide fine particles dispersed in an aqueous dispersion medium:
   a first type of titanium oxide fine particle which contains in solid solution a tin constituent and a transition metal constituent (exclusive of iron group constituents) that increases visible light responsiveness; and
   a second type of titanium oxide fine particle which contains in solid solution an iron group constituent, wherein each of the first type of titanium oxide fine particle and the second type of titanium oxide fine particle has an average particle size of from 5 to 30 nm, the average particle size being a volume-based 50% cumulative distribution size ($D_{50}$) measured by a dynamic laser light scattering, and
   the transition metal constituent in solid solution within the first type of titanium oxide fine particle is at least one selected from the group consisting of molybdenum and vanadium.

2. The visible light-responsive photocatalytic titanium oxide fine particle dispersion of claim 1, wherein the content of the tin constituent in the first type of titanium oxide fine particle, expressed as a molar ratio with titanium (Ti/Sn), is from 1 to 1,000.

3. The visible light-responsive photocatalytic titanium oxide fine particle dispersion of claim 1 or 2, wherein the transition metal constituent in solid solution within the first type of titanium oxide fine particle is molybdenum and vanadium.

4. The visible light-responsive photocatalytic titanium oxide fine particle dispersion of claim 1, wherein the content of the molybdenum constituent within the first type of titanium oxide fine particle, expressed as a molar ratio with titanium (Ti/Mo), is from 1 to 1,000 and the content of the vanadium constituent, expressed as a molar ratio with titanium (Ti/V) is from 10 to 10,000.

5. The visible light-responsive photocatalytic titanium oxide fine particle dispersion of claim 1, wherein the content of the iron group constituent within the second type of titanium oxide fine particle, expressed as a molar ratio with titanium (Ti/iron group constituent), is from 1 to 1,000.

6. The visible light-responsive photocatalytic titanium oxide fine particle dispersion of claim 1, wherein the iron group constituent in solid solution within the second type of titanium oxide fine particle is an iron constituent.

7. The visible light-responsive photocatalytic titanium oxide fine particle dispersion of claim 1, wherein the first type of titanium oxide fine particle and the second type of titanium oxide fine particle have a mixing ratio therebetween, expressed as the weight ratio [(first type of titanium oxide fine particle)/(second type of titanium oxide fine particle)], of from 99 to 0.01.

8. The visible light-responsive photocatalytic titanium oxide fine particle dispersion of claim 1, further comprising a binder.

9. The visible light-responsive photocatalytic titanium oxide fine particle dispersion of claim 8, wherein the binder is a silicon compound-based binder.

10. The visible light-responsive photocatalytic titanium oxide fine particle dispersion of claim 8, wherein the binder is at least one binder selected from the group consisting of a colloidal dispersion, a solution of a silicon compound, and an emulsion of a silicon compound.

11. The visible light-responsive photocatalytic titanium oxide fine particle dispersion of claim 8, wherein the binder is at least one binder selected from the group consisting of a colloidal silica, a silicate solution, a silane emulsion, a siloxane hydrolysate emulsion, a silicone resin emulsion, an emulsion of copolymer of a silicone-acrylic resin copolymer, and an emulsion of a silicone-urethane resin copolymer.

12. The visible light-responsive photocatalytic titanium oxide fine particle dispersion of claim 1, wherein the first type of titanium oxide fine particle and the second type of titanium oxide fine particle have a mixing ratio therebetween, expressed as the weight ratio [(first type of titanium oxide fine particle)/(second type of titanium oxide fine particle)], of from 9 to 1.

13. The visible light-responsive photocatalytic titanium oxide fine particle dispersion of claim 1, wherein each of the first type of titanium oxide fine particle and the second type of titanium oxide fine particle has the average particle size of from 11 to 30 nm.

14. A member having on a surface thereof a photocatalytic thin film formed by using the visible light-responsive photocatalytic titanium oxide fine particle dispersion of claim 1.

15. A method for producing the visible light-responsive photocatalytic titanium oxide fine particle dispersion of claim 1, comprising the steps of:
   (1) preparing a tin and transition metal-containing peroxotitanic acid solution from a starting titanium compound, a tin compound, a transition metal compound (exclusive of iron group compounds), a basic substance, hydrogen peroxide and an aqueous dispersion medium;
   (2) preparing a tin and transition metal-containing titanium oxide fine particle dispersion by heating the tin and transition metal-containing peroxotitanic acid solution prepared in Step (1) at from 80 to 250° C. under pressure control;
   (3) preparing an iron group element-containing peroxotitanic acid solution from a starting titanium compound, an iron group compound, a basic substance, hydrogen peroxide and an aqueous dispersion medium;
   (4) preparing an iron group element-containing titanium oxide fine particle dispersion by heating the iron group element-containing peroxotitanic acid solution prepared in Step (3) at from 80 to 250° C. under pressure control; and
   (5) mixing together the two titanium oxide fine particle dispersions prepared in Steps (2) and (4),
   wherein the transition metal constituent in solid solution within the first type of titanium oxide fine particle, prepared in Step (2), is at least one selected from the group consisting of molybdenum and vanadium.

* * * * *